United States Patent
Damaj

(10) Patent No.: US 10,758,505 B2
(45) Date of Patent: Sep. 1, 2020

(54) THERAPEUTIC COMPOSITIONS AND METHODS

(71) Applicant: Innovus Pharmaceuticals, Inc., San Diego, CA (US)

(72) Inventor: Bassam Damaj, San Diego, CA (US)

(73) Assignee: INNOVUS PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 15/829,798

(22) Filed: Dec. 1, 2017

(65) Prior Publication Data

US 2019/0167620 A1 Jun. 6, 2019

(51) Int. Cl.
| | |
|---|---|
| *A61K 31/198* | (2006.01) |
| *A61P 15/10* | (2006.01) |
| *A61K 9/48* | (2006.01) |
| *A61K 33/00* | (2006.01) |
| *A61K 31/4415* | (2006.01) |
| *A61K 31/443* | (2006.01) |
| *A61K 47/02* | (2006.01) |
| *A61K 47/38* | (2006.01) |

(52) U.S. Cl.
CPC .............. *A61K 31/198* (2013.01); *A61K 9/48* (2013.01); *A61K 9/4875* (2013.01); *A61K 31/443* (2013.01); *A61K 31/4415* (2013.01); *A61K 33/00* (2013.01); *A61K 47/02* (2013.01); *A61K 47/38* (2013.01); *A61P 15/10* (2018.01); *A61K 9/4866* (2013.01)

(58) Field of Classification Search
CPC ......... A61K 31/198; A61P 15/10; A61P 15/12
See application file for complete search history.

(56) References Cited

U.S. PATENT DOCUMENTS

| | | | |
|---|---|---|---|
| 5,536,506 A | | 7/1996 | Majeed et al. |
| 5,744,161 A | * | 4/1998 | Majeed ................ A61K 9/0014 424/423 |
| 7,262,192 B2 | | 8/2007 | Bell et al. |
| 9,161,565 B1 | | 10/2015 | Bezzek |
| 2001/0008641 A1 | * | 7/2001 | Krotzer ................. A61K 45/06 424/725 |
| 2008/0305096 A1 | * | 12/2008 | Verdegem .............. A61K 9/148 424/94.4 |
| 2009/0143433 A1 | | 6/2009 | Hendrix |

(Continued)

FOREIGN PATENT DOCUMENTS

| | | |
|---|---|---|
| EP | 0810868 B1 | 8/2001 |
| EP | 2027857 A2 | 2/2009 |

(Continued)

OTHER PUBLICATIONS

"Astragin" Product Insert pdf, NuLiv Science, www.nulivscience.com. (Year: 2018).*

(Continued)

*Primary Examiner* — Craig D Ricci
*Assistant Examiner* — Janet L. Coppins
(74) *Attorney, Agent, or Firm* — Sheridan Ross P.C.

(57) ABSTRACT

The invention provides compositions and unit dosage forms that are effective to improve sexual performance. Such compositions and unit dosage forms are useful to increase duration of sexual intercourse, satisfaction with sexual intercourse, and improve erectile function in men.

1 Claim, 4 Drawing Sheets

(56) References Cited

U.S. PATENT DOCUMENTS

2016/0106793 A1    4/2016   Peltier et al.
2018/0325903 A1   11/2018   Damaj

FOREIGN PATENT DOCUMENTS

WO    2015048590 A1    4/2015
WO    2015061860 A1    5/2015

OTHER PUBLICATIONS

CAS Registry Listing for Piperine, RN 94-62-2, published Nov. 16, 1984. (Year: 1984).* https://www.NUTRAIngredients-usa.com/Article/2012/03/26NuLiv-Science-annouces-self-affirmed-GRAS-for-AstraGin-ingredient# (Year: 2012).*

U.S. Appl. No. 15/979,120, US 2018-0325903.
U.S. Appl. No. 15/829,799.
U.S. Appl. No. 15/829,797.
U.S. Appl. No. 15/829,801.
U.S. Appl. No. 15/829,822.

Awad, et al., "Effect of beta-sitosterol, a plant sterol, on growth, protein phosphatase 2A, and phospholipase D in LNCaP cells", Nutr Cancer 36(1), 74-78 (2000) Abstract, 2 pages.

Fry, et al., "Impact of Nitric-oxide-mediated vasodilation and oxidative stress on renal medullary oxygenation: modeling study", Am J Physiol Renal Physiol 310, F237-F247 (2016).

Life Extension, "All About Supplements—Pygeum", http://222.lifeextension.com/magazine/2006/4/aas/page-01, 5 pages, retrieved on Sep. 24, 2018.

Manukhina, et al., "General Pathology and Pathophysiology. Role of Nitric Oxide in Prevention of Cognitive Disorders in Neurodegenerative Brain Injuries in Rats", Bulletin of Experimental Biology and Medicine 146(4), 391-395 (2008).

Mascio, et al., "Lycopene as the most efficient biological carotenoid singlet oxygen quencher", Archives of Biochemistry and Biophysics 274(2), 532-538 (1989). Abstract, 2 pages.

Mehmood, et al., "Black Pepper and Piperine Possess Antidiarrheal Effect Mediated Through Phosphodiesterase Inhibitory and CA++ Antagonist Pathways", Basic & Clinical Pharmacology & Toxicology 1 (Suppl 1) Abstract # 834, 256 (2014).

Morris, "Arginine Metabolism: Enzymology, Nutrition, and Clinical Significance. Enzymes of Arginine Metabolism", J Nutri 134, 2743S-2747S (2004).

Mukhtar, et al., "Green Tea in Chemoprevention of Cancer", Toxicological Sciences 52 (Supplement), 111-117 (1999).

Perva-Uzunalic, et al., "Extraction of active ingredients from green tea (Camellia sinensis): Extraction efficiency of major catechins and caffeine", Food Chemistry 96, 597-605 (2006).

Puritan's Pride, "Arginine", Citrulline complex capsules from Puritan's Pride, 3 pages (2013).

Recalmax, Product Insert, Innovus Pharmaceuticals, Inc., 3 pages (Oct. 2016).

Riehemann, et al., "Plant extracts from stinging nettle (Urtica dioica), an antirheumatic remedy, inhibit the proinflammatory transcription factor NF-kB", FEBS Letters 442, 89-94 (1999).

Simon, et al., "Decoding the Substrate Supply to Human Neuronal Nitric Oxide Synthase", PLOS One 8(7), e67707, 12 pages (2013).

Vesele, Product Insert, Innovus Pharmaceuticals, Inc., 3 pages (Oct. 2016).

Webmd, "Saw Palmetto", https://www.webmd.com/vitamins/ai/ingredientmono-971/saw-palmetto, 4 pages, retrieved on Sep. 24, 2018.

* cited by examiner

THERAPEUTIC COMPOSITIONS AND METHODS

BACKGROUND OF THE INVENTION

The World Health Organization defines Sexual Health as: " . . . a state of physical, emotional, mental and social well-being in relation to sexuality; it is not merely the absence of disease, dysfunction or infirmity".

Common sexual health conditions in men are:
Anejaculation—Unable to ejaculate semen
Delayed Ejaculation—Difficulty ejaculating
Erectile Dysfunction—Inability to achieve or maintain an erection
Premature Ejaculation—Ejaculating earlier than desired
Retrograde Ejaculation—Semen travels into the bladder during ejaculation
Low Testosterone—Inadequate production of testosterone In particular, Premature Ejaculation (PE), also referred to as 'early ejaculation' or 'rapid ejaculation', is ejaculation with minimal penile stimulation shortly after sexual intercourse or even before intercourse. Premature ejaculation may be defined as ejaculating within one minute or less after sexual intercourse and is the most prevalent sexual dysfunction affecting men across all age groups. One in five men in America suffers from PE, mostly affecting men between the ages 18 and 59 years old. The prevalence is estimated at 41%. The two types of PE are: Primary PE: The most common type: Problem present from the beginning of the man's sexual life, and Secondary PE which occurs suddenly at some point in a man's life. It is estimated that 9 out of 10 men ejaculate within 1 minute of penetration. The causes of PE include: psychological conditions such as anxiety, depression, overexcitement; and biological effects from drug use, prostate disease, multiples sclerosis, diabetes, inflammation of the prostate and urethra, hormone levels, and low levels of serotonin.

PE negatively affects sexual enjoyment and a man's ability to satisfy his partner resulting in:
Low self-esteem
Frustration and depression
Withdrawal leading to a strenuous relationship
Loss of interest in sex One out of every three men feel that they ejaculate too soon and wish they could increase the length of arousal before ejaculation. A need exists for safe and effective supplements to treat such sexual health conditions.

SUMMARY OF THE INVENTION

The beneficial effects of the present invention are surprising and unexpected to support and enhance peak sexual performance. A synergistic composition of vitamin B6 (vitamin), magnesium (mineral) and 4 amino acids, the present invention is formulated with two proprietary absorption enhancing ingredients. Regular use of the present invention is well tolerated, gives no drug side effects, and has been clinically evaluated in multiple studies.

Applicant has determined that men taking the present invention in the disclosed unit dosage forms report improvements in sexual performance, including increased duration of sexual intercourse, increased satisfaction with sexual intercourse, and improved erectile function.

DETAILED DESCRIPTION

Figure 1:
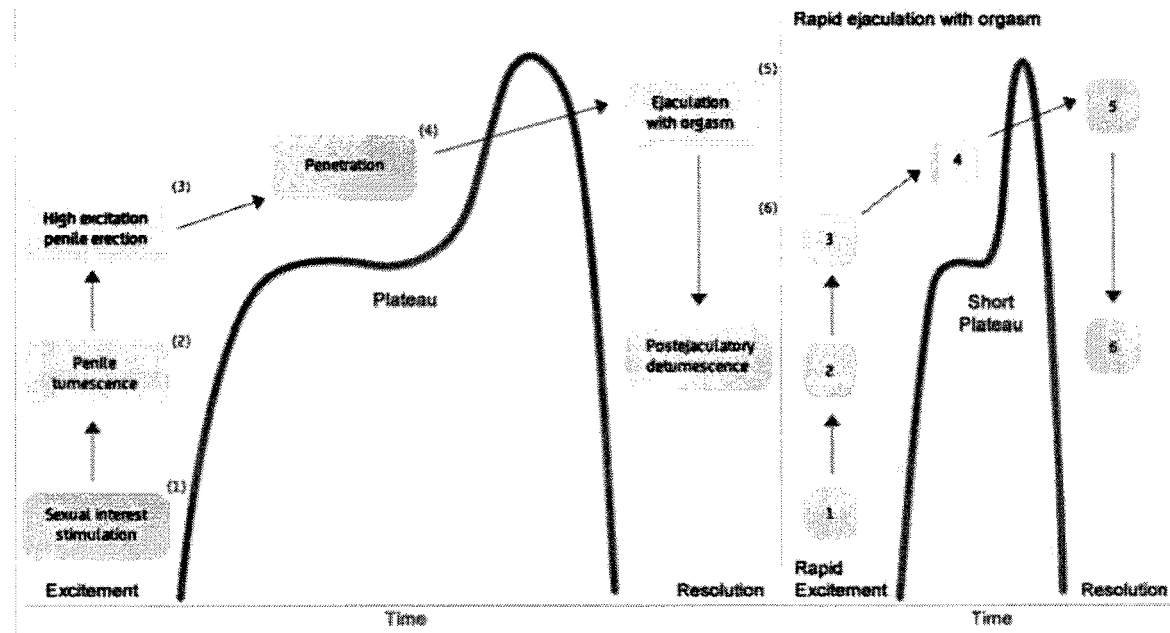
FIG. 1 shows the Ejaculation Sequence of events for Normal Ejaculation (left) and Premature Ejaculation (right).

As used herein, the term "about" has its generally accepted meaning. In one embodiment, the term about means ±10% of the associated value. For example, about 100 mg means 100 mg±10 mg. In one embodiment, the term about means ±5% of the associated value. For example, about 100 mg means 100 mg±5 mg. In one embodiment, the term about means ±2% of the associated value. For example, about 100 mg means 100 mg±2 mg. In one embodiment, the term about means ±1% of the associated value. For example, about 100 mg means 100 mg±1 mg.

The present invention has been developed as a dietary supplement to support peak sexual performance and stamina.

In one embodiment, a unit dosage form of the invention may contain one or more pharmaceutical diluents or excipients. For example, in one embodiment a unit dosage form of the invention may comprise microcrystalline cellulose, silicon dioxide, and magnesium stearate. In another embodiment a unit dosage form of the invention comprises one or more excipients selected from hydroxypropyl methylcellulose, rice concentrate, and silica.

The amino acids in the present invention includes L-tyrosine, DL-phenylalanine, L-typtophan, L-glutamine, Vitamin B6, magnesium, piperylpiperidine, and an absorption enhancer. L-Tyrosine is a precursor for the synthesis of important biologically active substances, including the Catecholamines (dopamine, adrenaline, noradrenaline) and thyroid hormones. L-Tyrosine may support alertness and regulate stress and moods.

DL-phenylalanine is an essential amino acid supporting important biochemical processes in the body by helping the brain develop active chemicals-endorphins, improving mood, increasing the number of receptors to endorphins in the brain, and supporting optimum energy levels.

L-tryptophan is an essential amino acid converted into serotonin connection, which contributes to the duration of sexual intercourse and is required for the synthesis of melatonin (regulation of human biorhythms).

L-glutamine is required to formulate a number of important vitamins and contributes to efficient muscle growth, ensures nervous activity and maintaining the immune system, and promotes serotonin synthesis, necessary to ensure the normal duration of sexual intercourse.

Vitamin B6 (pyridoxine hydrochloride) is required for the synthesis of serotonin which supports the duration of sexual intercourse. Vitamin B6 is also a catalyst for exchange of amino acids and synthesis of neurotransmitters of the central nervous system, resulting in an improved the metabolism in tissues of the brain and a uniform supply of cells to glucose. Vitamin B6 is required for the regulation of (L)-tyrosine.

Magnesium in the form of a magnesium salt, such as magnesium oxide, is an important component for the biosynthesis of proteins, as well as for ensuring the processes of excitability and contractility in the nerve elements of muscle tissue. Magnesium is a regulator of the passing of redundant nerve impulses from the brain to peripheral nerves and muscles, prevents excessive spasms (involuntary muscle contractions), including sexual system.

Magnesium and vitamin B6 together show a more significant efficiency and at lower doses than when used separately.

PEVArx™ contains two natural absorption enhancing ingredients to increase bioavailability:

AstraGin® is a patented Absorption Enhancer, and a 100% natural food ingredient derived from highly purified *Panax notoginseng* and *Astragalus membrenaceus*. Studies indicate increases in amino acid, vitamin and mineral absorption.

Bioperine® is a patented Absorption Enhancer, obtained from black pepper fruits (*Piper nigrum*). Bioperine® helps the body absorb the amino acids (see U.S. Pat. No. 5,536,506 and European Patent EP0810868B1). Bioperine® (extract) inhibits human CYP3A4 and P-glycoprotein enzymes. By inhibiting certain enzymes Bioperine® (extract) may alter the effectiveness of certain medications by increasing bioavailability. Bioperine is Generally Recognized As Safe (GRAS). Bioperine® (CAS Reg. No. 94-62-2) is named as 1-piperylpiperidine; 5-(1,3-benzodioxol-5-yl)-1-(piperidin-1-yl)penta-2,4-dien-1-one; and (2E,4E)-5-(1,3-benzodioxol-5-yl)-1-(piperidin-1-yl)penta-2,4-dien-1-one, and has the structure:

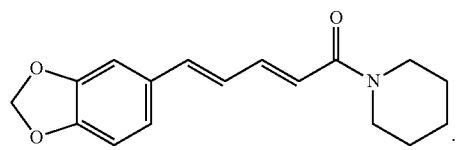 [SMILES: O=C(/C=C/C=C/c1ccc2c(c1)OCO2)N1CCCCC1]

Studies indicate absorption of nutrients are enhanced by at least 30% with PEVArx™

TABLE 1

| | PEVArx ™ Product Profile |
|---|---|
| Use | Support sexual performance and duration |
| Composition | Vitamin B6 |
| | Mineral: Magnesium |
| | Amino Acids: L-Tyrosine, DL-Phenylalanine, L-Tryptophan, L-Glutamine |
| Dosing and Administration | Adults, 2 capsules/2 times per day with meal |
| Packaging/Storage and Handling | 60 capsules per container |
| | Store between 20-25 C. (65-77 F.) |
| | 3 year shelf life |

TABLE 1-continued

| | PEVArx ™ Product Profile |
|---|---|
| Safety and efficacy Warnings/Caution | Clinically studied and well tolerated |
| | Intended for adult men |
| | Keep out of reach of children |
| | Consults with physician before use, especially if hypertensive |

Efficacy of PEVArx™ was studied in a pilot, placebo controlled study (2011) in a Population of 43 men with PE, 24-67 years of age (37.9±1.2). The Study duration was 3 months. Results indicated the Duration of sexual intercourse in the treatment group increased on average from 0.9 minute to 3.5 minutes (p<0.05) in 67.8% of patients. The efficacy and safety of PEVArx™ was studied in an open label, multicenter study (2013) Population: Men with reported rapid ejaculation. Nine sites reported results of increased length of penetration phase on average by 2.5 times, and improved sexual function as a whole and overall wellbeing.

PEVArx™ Clinical Study: The efficacy and safety of PEVArx™ was studied in a multicenter, non-interventional (observational) study in men with sexual dysfunction. Population: 665 men with sexual dysfunction (analysis on 630 patients). Clinical sites: 23 centers. Duration: 2 months. Study design: Observational. Study article: PEVArx™—two (2) capsules taken twice daily (oral). Inclusion: Sexual dysfunction (PE ED, anxiety, erosion of orgasm). Exclusion: Contraindication for study article, acute psychiatric symptoms.

Measurement Tools:
    Individual registration card (IRK)
    Concomitant therapy information
    Hospital anxiety and depression scale (HADS)
    Modified IIEF to measure ejaculatory function
    Analysis of the PEVArx™ Clinical Study Data
    The Data is divided into three groups:
    Group 1: PE (rapid ejaculation) Self-reported (N=582/92.4%)
    Group 2: Orgasmic disorder (N=17/2.7%)
    Group 3: Urologic disease (inflammatory disease of the prostate, ED, BPH etc.) secondary to anxiety (N=31/4.9%)
    Evaluation of PEVArx™ Effectiveness:
    Duration of penetration phase of sexual contact time was evaluated on the grading scale:
    Pronounced effect: >50% increase in duration
    Good effect 30-49% increase in duration
    Satisfactory effect: 10-29% increase duration
    An unsatisfactory effect: absence of positive dynamics of the patient or the patient's degradation
    Data Analysis PEVArx™ Effectiveness on Duration:

Effectiveness of treatment in patients during penetration phase of sexual contact (duration time) showed the following in Tables 2 and 3.

TABLE 2

| | All groups | | | | |
|---|---|---|---|---|---|
| | Visit 2 | | Visit 3 | | |
| Grade | (n) | % | (n) | % | (p)$_{2-3}$ |
| Pronounced | 358 | 60.6 | 470 | 81.0 | 0.00 |
| Good | 54 | 9.1 | 34 | 5.9 | 0.052 |

TABLE 2-continued

| | All groups | | | | |
|---|---|---|---|---|---|
| | Visit 2 | | Visit 3 | | |
| Grade | (n) | % | (n) | % | $(p)_{2-3}$ |
| Satisfactory | 35 | 5.9 | 19 | 3.3 | 0.014 |
| Unsatisfactory | 144 | 24.4 | 57 | 9.8 | 0.00 |
| Total | 591 | | 580 | | |

TABLE 3

| | Group 1: PE Patients | | | | |
|---|---|---|---|---|---|
| | Visit 2 | | Visit 3 | | |
| Grade | (n) | % | (n) | % | $(p)_{2-3}$ |
| Pronounced | 344 | 61.9 | 451 | 82.8 | 0.00 |
| Good | 50 | 9.0 | 32 | 5.9 | 0.06 |
| Satisfactory | 34 | 6.1 | 16 | 2.9 | 0.017 |
| Unsatisfactory | 128 | 23.0 | 46 | 8.4 | 0.00 |
| Total | 556 | | 545 | | |

TABLE 4

| PEVArx ™ Adverse Events | | | | | |
|---|---|---|---|---|---|
| Adverse events related to PEVArx | | | Adverse events possibly related to PEVArx | | |
| AE | N | % | AE | N | % |
| Mild allergic reaction | 1 | 0.16 | Neuralgia, nausea | 4 | 0.63 |
| Hyperemia | 1 | 0.16 | Perineal discomfort | 2 | 0.32 |
| Drowsiness | 3 | 0.47 | Heart rate increases slightly | 1 | 0.16 |
| Dry cough | 1 | 0.16 | | | |
| Total | 6 | 0.95 | Total | 7 | 1.1 |

In summary, PEVArx™ Clinical Study Results show:

Efficacy
- Penetration duration: 91.6% of patients in Group 1 (PE population) reported an increase on average of 2.5 times at end of study
- Overall patient satisfaction: On average, 3 times increase in all groups
- IIEF domains: Statistically significant improvement of sexual function of patients on virtually all domains
- Anxiety-depressive symptoms: Decrease on symptoms HADS (Hospital Anxiety and Depression score) in 90% of the patients.
- Concomitant medications: A notable decline in continued use of other medicines and dietary supplements (Group1 decreased from 21.9% to 12.7% by end of study)

Safety
- Well tolerated both alone and in combination with other drugs

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

FIG. 1 shows the differences in the ejaculation sequence of events for normal ejaculation (left graph) and premature ejaculation (right graph). As evidenced by the difference between the two graphs, men suffering from premature ejaculation have a short plateau where the penetration phase occurs. A controlled study of the formula has been shown to increase the length of the penetration phase on average by 2.5 times. By increasing the length of penetration, the plateau shown on the graph lengthens and the sexual experience occurs more like the sequence of events for normal ejaculation (left graph).

Figure 2:
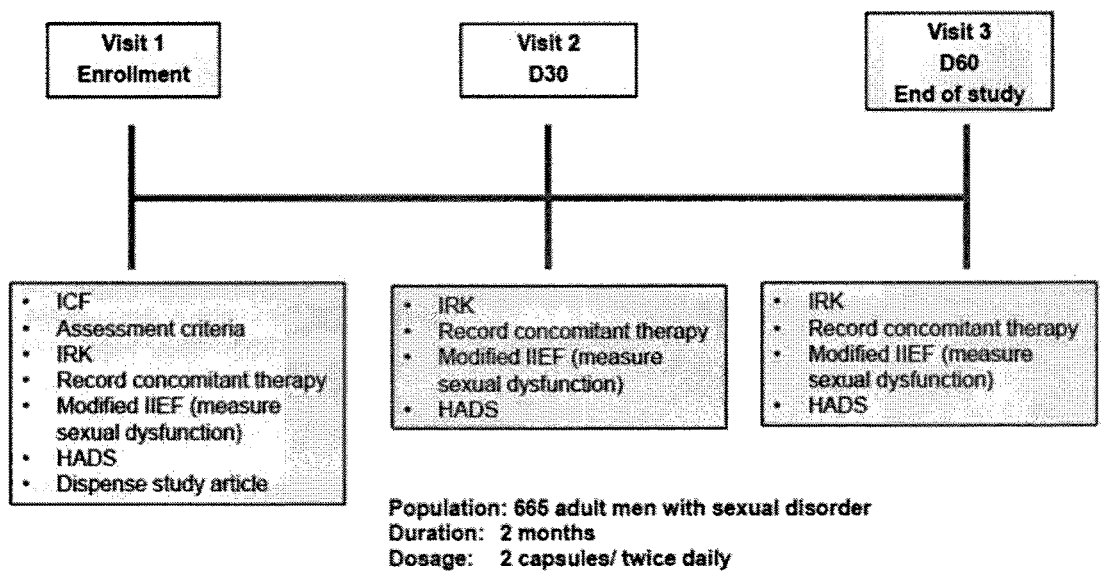
FIG. 2 shows the design of the clinical study testing the present invention.

FIG. 2 shows the clinical study design. During the first visit, the patient is enrolled in the program, the participant fills out an informed consent form (ICF), provides assessment criteria to determine whether the patient can provide useful feedback on the formula, fills out an individual registration card (IRK), and any concomitant therapy is recorded. Further, the participant's Modified International Index of Erectile Function (IIEF) and Hospital Anxiety and Depression Scale (HADS) is measured and recorded for future comparison. During the first visit the study article is dispensed for the patient's own personal information about the formula.

During the second and third visits, the patient fills out the individual registration card and the Irk is recorded. The Modified IIEF and HADS of the patient is recorded for comparison with any past and future visits. This clinical trial involved a population of 665 adult men with sexual disorder for a duration of 2 months. Each participant took a dosage of two capsules twice per day for a total of four capsules per day.

Figure 3:
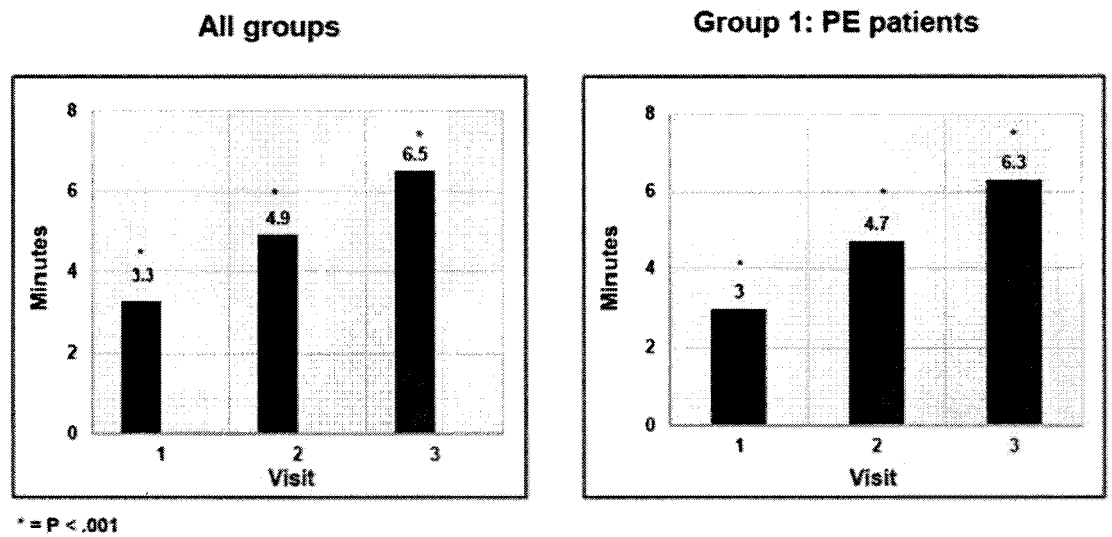
FIG. 3 shows the Mean Duration of Sexual Intercourse experienced by participants in the clinical study as recorded over three visits.

FIG. 3 shows the mean duration of sexual intercourse for the clinical trial participants. The left graph shows the effect that the formula has on all groups. During the first visit, the average participant had a mean duration of sexual intercourse of 3.3 minutes which increased to 4.9 and 6.5 minutes respectively during additional visits. For participants experiencing premature ejaculation, the average participant experienced an average of 3.0 minutes of sexual intercourse which increased to 4.7 and 6.3 minutes respectively during additional visits. This set of graphs demonstrates that the duration of sexual doubled between the first and third visits for those experiencing premature ejaculation. Furthermore, all participants in the study, including this with and without premature ejaculation, reported an average increase of three minutes duration of sexual intercourse between the first and third visits.

Figure 4:
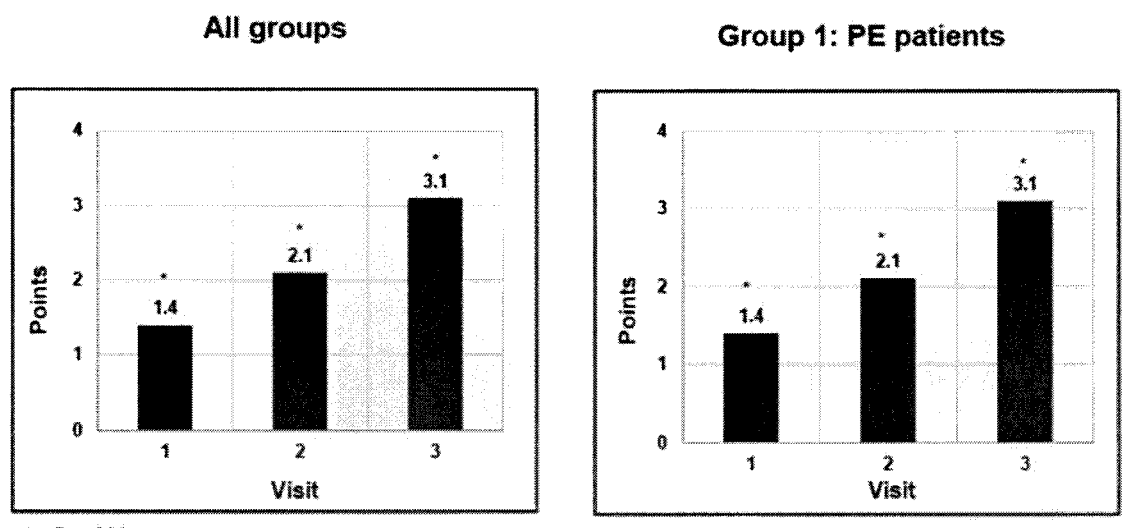
FIG. 4 shows Mean Satisfaction with Sexual Intercourse experienced by participants in the clinical study as recorded over three visits.

FIG. 4 shows the mean satisfaction with sexual intercourse experienced by the clinical trial participants. For this measurement, participants from all groups and only the group of participants experiencing premature ejaculation reported the same mean score for all three visits. Both groups reported a mean score of 1.4 during the first visit and the score increased to 2.1 and 3.1 respectively during the following visits for an overall increase of 1.7 from all groups. This set of graphs demonstrates that men taking the recommended dose of the claimed formula experienced over double the satisfaction with sexual intercourse.

Figure 5:
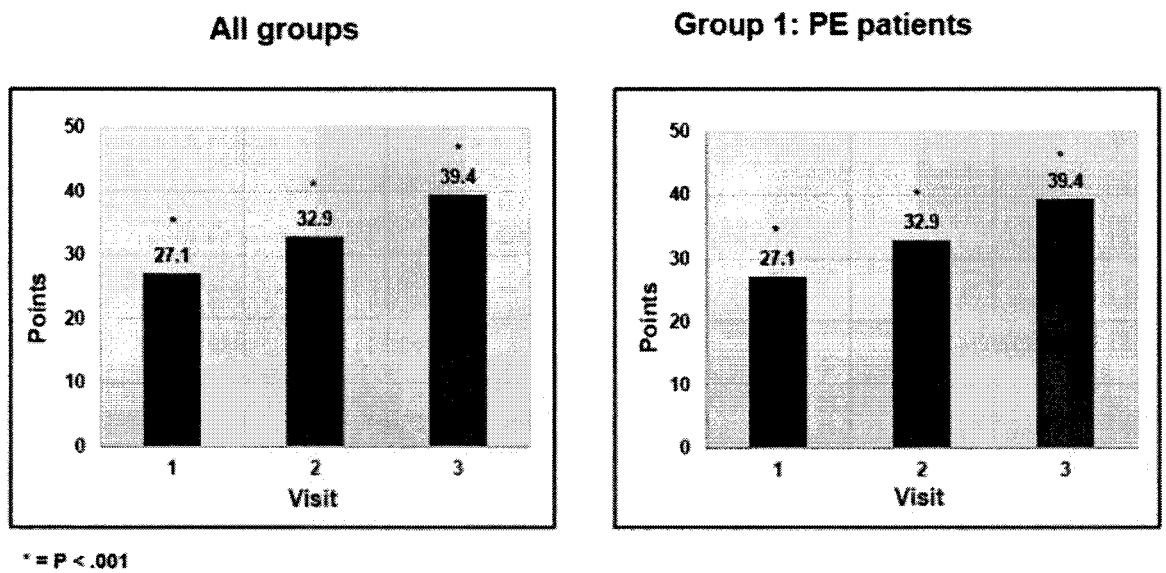
FIG. 5 shows Mean IIEF (International Index of Erectile Function) Sum of Points experienced by participants in the clinical study as recorded over three visits.
Figure 6:
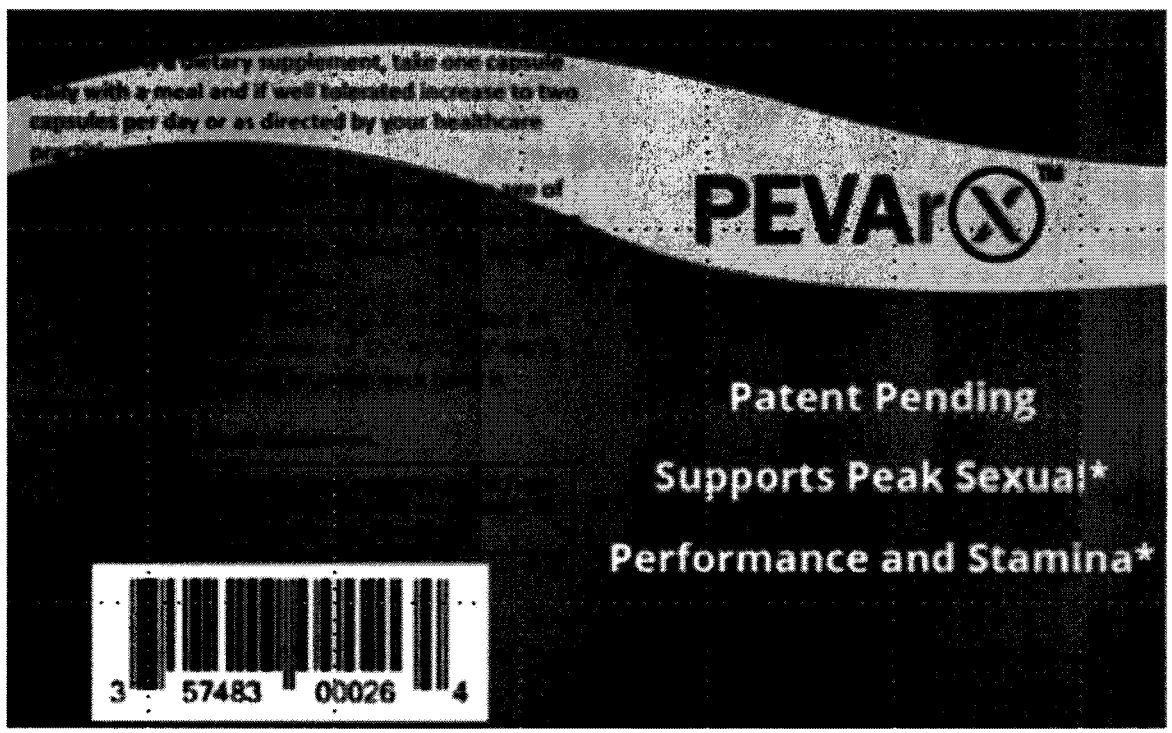
FIG. 6 shows PEVArx™ labeling indicates:
Support longer sexual performance
Supported by clinical trials
Synergistic formulation to support sexual performance
Daily support
Increased absorption
Well tolerated
Figure 7:
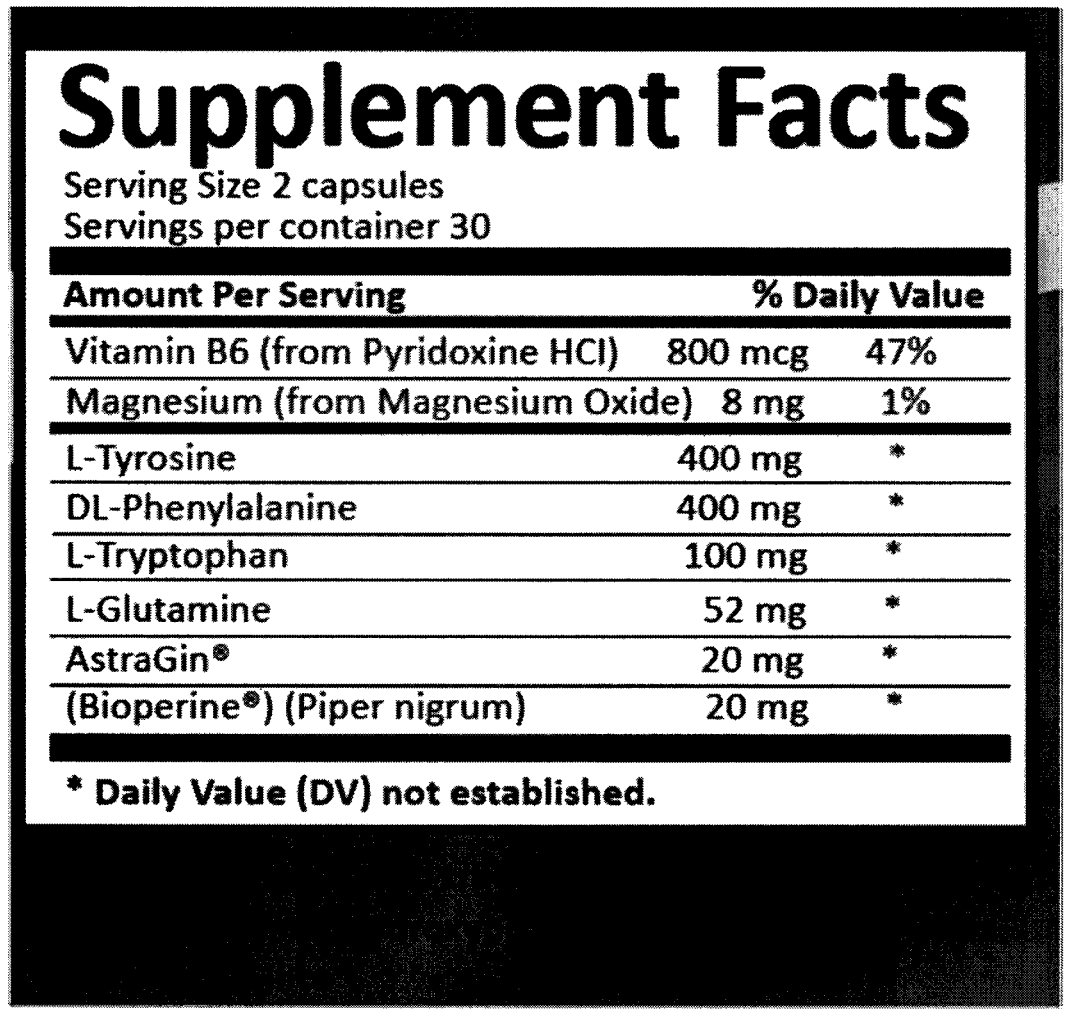
FIG. 7 shows the PEVArx™ Supplement Facts Box:
One month supply
Synergistic vitamin and mineral combination
Four amino acids to support longer sexual performance
Two patented absorption enhancers: AstraGin® and Bioperine®

FIG. 5 shows the mean International Index of Erectile Function (BEF) sum of points experienced by the clinical trial participants. For this measurement, participants from all groups and the group of participants experiencing premature ejaculation reported the same mean score for all three visits. Both groups reported a mean score of 27.1 for the first visit and the score increased to 32.9 and 39.4 respectively during subsequent visits. As a result, this set of graphs demonstrates that both the total group of participants and those participants experiencing premature ejaculation experienced a mean total increase of 12.3 points on the IIEF scale between the first and third visits.

What is claimed is:

1. A unit dosage form suitable for oral administration in a human comprising:
   about 800 μg Vitamin B6;
   about 8 mg Mg+2, from magnesium oxide;
   about 400 mg L-tyrosine;
   about 400 mg DL-phenylalanine;
   about 100 mg L-tryptophan;
   about 52 mg L-glutamine;
   about 20 mg AstraGin®; and
   about 20 mg 1-piperylpiperidine; and
   further comprising one or more excipients selected from hydroxypropyl methylcellulose, rice concentrate, and silica;
   wherein the unit dosage form is formulated as a capsule.

* * * * *